United States Patent [19]

Morley et al.

[11] Patent Number: 5,719,123
[45] Date of Patent: Feb. 17, 1998

[54] CICLOSPORIN FORM FOR PULMONARY ADMINISTRATION

[75] Inventors: John Morley, Muttenz, Switzerland; Andreas Rummelt, Lörrach, Germany; Martin List, Basel, Switzerland

[73] Assignee: Sandoz Ltd., Basel, Switzerland

[21] Appl. No.: 254,094

[22] Filed: Jun. 6, 1994

Related U.S. Application Data

[63] Continuation of Ser. No. 128,444, Sep. 28, 1993, abandoned, which is a continuation of Ser. No. 852,597, Mar. 17, 1992, abandoned.

[30] Foreign Application Priority Data

Mar. 18, 1991 [GB] United Kingdom ............ 9105705

[51] Int. Cl.$^6$ ................................. A61K 38/13
[52] U.S. Cl. .................. 514/11; 514/15; 530/328; 530/333
[58] Field of Search ................. 514/15, 11; 530/328, 530/333

[56] References Cited

FOREIGN PATENT DOCUMENTS 2211848  12/1989  United Kingdom ............ C07K 7/64

OTHER PUBLICATIONS

Dowling et al., Surgery, vol. 108, No. 2 (1990) PP. 198–205.

*Primary Examiner*—Howard E. Schain
*Attorney, Agent, or Firm*—Robert S. Honor; Melvyn M. Kassenoff; Thomas O. McGovern

[57] ABSTRACT

Pulmonary administration of Ciclosporin in orthorhombic crystal form (designated "CY-A/X-III"), e.g. for the treatment of obstructive or inflammatory airways disease, e.g. asthma, as well as crystalline Ciclosporin, e.g. CY-A/X-III, in spheroidal particulate form, processes for its preparation and its pharmaceutical use, e.g. for pulmonary administration. Pharmaceutical compositions comprising CY-A/X-III and crystalline Ciclosporin, e.g. CY-A/X-III, in spheroidal particulate form as well as Ciclosporin in solution in aerosol propellants are also provided.

13 Claims, No Drawings

CICLOSPORIN FORM FOR PULMONARY ADMINISTRATION

This is a continuation of application Ser. No. 08/128,444, filed Sep. 28, 1993, now abandoned, which in turn is a continuation of application Ser. No. 07/852,597, filed Mar. 17, 1992, now abandoned.

The present invention relates to novel pharmaceutical uses of and novel pharmaceutical compositions comprising Ciclosporin in non-solvate orthorhombic crystal form as well as to a novel form of crystalline Ciclosporin and further novel pharmaceutical compositions comprising Ciclosporin.

Ciclosporin, also known as cyclosporin A, is the drug substance of formula

Ciclosporin is known and commercially available under the Registered Trade Mark SANDIMMUN® or SANDIMMUNE®.

In the solid state, Ciclosporin exists in both amorphous and crystalline form. In the crystalline state various modifications exist. In a first aspect the present invention relates to Ciclosporin in the crystal form designated "CY-A/X-III". By "CY-A/X-III" as used herein and throughout the accompanying claims is meant Ciclosporin in non-solvate orthorhombic ($P2_12_12_1$) crystal form.

CY-A/X-III is described and claimed together with processes for its production in GB patent publication no. 2 211 848 (A) (application no. 88 295563, filing date=Dec. 19, 1988, publication date=Jul. 12, 1989) and equivalents world-wide, including e.g. New Zealand patent application no. 227384.

As disclosed in the said UK patent publication, the dimensions of the crystal lattice of CY-A/X-III are: a=12.7 Å, b=15.7 Å, c=36.3 Å. The volume per asymmetric unit= 1804 Å$^3$. CY-A/X-III exhibits the following X-ray powder diffraction characteristics, e.g. as determined employing a Guinier-DeWolff II camera, using CuKα-radiation, λ=1.542 Å:

| Line No. | d (Å) | Intensity |
| --- | --- | --- |
| 1. | 12.0 | M |
| 2. | 10.4 | VS |
| 3. | 9.6 | S |
| 4. | 8.7 | S |
| 5. | 7.9 | M |
| 6. | 7.7 | S |
| 7. | 6.7 | M |
| 8. | 6.0 | M |
| 9. | 5.83 | S |
| 10. | 5.3 | M |
| 11. | 5.2 | M |
| 12. | 4.92 | S |
| 13. | 4.88 | S |
| 14. | 4.58 | M |
| 15. | 4.48 | M |
| 16. | 4.0 | M |
| 17. | 3.59 | M |
| 18. | 3.38 | M |

VS = very strong, S = strong, M = medium.

CY-A/X-III has a melting point of ca. 180°–195° C.

As discussed in the said UK patent publication, Ciclosporin is used, or has been proposed for use, clinically as an immunosuppressive agent for the treatment of recipients of organ transplants and for the treatment of a wide variety of autoimmune diseases. Further areas of investigation have included potential applicability as an anti-parasitic agent as well as use in reversing tumor resistance to chemotherapeutic, e.g. cytostatic, drug therapy and in promoting hair growth.

More recently Ciclosporin has further been found to be effective in the treatment of obstructive or inflammatory airways disease, notably asthma. Controlled clinical trials involving oral administration of Ciclosporin to asthmatics, e.g. asthmatics resistant to or dependent on steroid asthma therapy, have been proposed and now reported in the literature: see e.g. Czczecklik et al., Allergy, 46 Art. 072, (1991) and Alexander et al., Lancet 339 (Feb. 8, 1992) p. 324 and further references cited therein.

Reports have also appeared in the literature describing administration of Ciclosporin, in particular in animal lung transplantation models, by the pulmonary route: see e.g. Dowling et al., Surgery (St.Louis) 108, (2), 198–205 (1990); Zenati et al., J. Heart Transplant 9, (1), 64 (1990); Muggerburg et al., Am. Rev. Resp. Dis., 139 (4/Pt 2), A 267 (1989); and Burckart et al., J. Clin. Pharmacol., 29, (9), 860 (1989). Suppression of eosinophil infiltration of the airways following pulmonary administration of micronised Ciclosporin in experimental animal asthma models has also been described: see e.g. Boubeckeur et al. Eur. J. Pharmacol., 183 (4), 1187–1188 (1990).

In accordance with the teachings of the aforementioned UK patent publication no. 2 211 848, CY-A/X-III is proposed for use as active principle in Ciclosporin containing galenic formulations. Specific formulations suggested include topical forms for dermal or ophthalmic application and injectible forms for infusion, intra-lesional injection (e.g. in the treatment of psoriasis) and intra-articular injection (e.g. in the treatment of inflammatory/autoimmune disease of the joints, for example, rheumatoid arthritis). Galenic formulations for enteral administration are also proposed.

The present invention is based in one aspect upon the finding that CY-A/X-III has surprising and unexpected benefit when administered by the pulmonary route.

As already discussed, use of orally administered Ciclosporin for treatment of airways disease, for example asthma, is known. For the treatment of pulmonary disease, e.g. asthma, oral administration of Ciclosporin however has evident disadvantages. Ciclosporin is a potent immunosuppressive drug, and as such may cause a general lowering of the body's immune response following systemic resorption. Such an effect is clearly undesirable in subjects, for example, asthmatics, whose condition may be consequential to, or precipitated or exacerbated by, infection, e.g. pulmonary tract infection. In addition, oral administration of Ciclosporin carries with it the known risk of undesirable systemic side-effect, for example renal-dysfunction, following long-term usage.

To meet such difficulty, a means of local administration to the airways and lungs with the avoidance, as far as possible, of systemic drug resorption would be an evident desideratum. However local administration of Ciclosporin to the airways and lungs presents numerous problems.

First, Ciclosporin is highly hydrophobic and carrier media available for its galenic formulation, e.g. vegetable oils and the like, are inappropriate for use in an inhaled form. Secondly, there is the problem inherent in any pulmonary/ inhaled delivery system, that a major percentage of the administered drug substance does not enter the airways and lungs, but remains trapped in the buccal cavity, or on the membranous surfaces of the pharynx, subsequently to be swallowed into the stomach. In patients with compromised lung function, e.g. asthmatics, this problem is especially acute. Controlled trials have shown that when dry substances are administered to such subjects by inhalation, the greater part of the administered drug, up to 80% or more, in fact enters the gastro-intestinal tract. The risk of regular systemic resorption and side-effect following pulmonary administration of Ciclosporin thus remains. Thirdly, there is the problem of providing a form which will be effective in treating the desired disease within the airways and lung, i.e. which is active at the intended site of delivery.

In accordance with the present invention it has now surprisingly been found that CY-A/X-III provides means for the local delivery of Ciclosporin to the airways and lungs which meet the above difficulties and is advantageously effective and beneficial for such use.

Specifically CY-A/X-III provides Ciclosporin in a form inherently adapted or adaptable to pulmonary administration and which is highly effective in treating disease or other adverse conditions of the lungs or airways, both in terms of potency and duration of action. Specifically CY-A/X-III provides a form of Ciclosporin which is unexpectedly better suited to pulmonary administration and distribution at the lung surfaces as compared with other forms of Ciclosporin. Yet more surprisingly, it has been found that the use of CY-A/X-III for pulmonary administration restricts the risk of systemic resorption and consequential side effect, for example following unavoidable or inadvertant systemic delivery, e.g. through swallowing, as compared with use of Ciclosporin in other form.

Pulmonary administration of CY-A/X-III as well as the tratment of diseases or conditions of the airways or lungs by pulmonary administration of CY-A/X-III is new. The present invention accordingly provides:

$A^1$ A method for the administration of Ciclosporin by the pulmonary route which method comprises pulmonary administration of CY-A/X-III;

$A^2$ A method of effecting Ciclosporin therapy for the treatment of any disease or condition of the airways or lungs requiring such therapy, comprising pulmonary administration of CY-A/X-III;

or, in the alternative:

$A^3$ CY-A/X-III for use in the preparation of a pharmaceutical composition for pulmonary administration.

The invention comprises pulmonary administration of CY-A/X-III, that is administration of CY-A/X-III via the pulmonary route, e.g. by inhalation. The CY-A/X-III is thereby delivered into the airways and lung to effect topical administration within the airways or lung.

The invention provides means for effecting Ciclosporin therapy of the airways or lung. The invention may be applied in the treatment of any subject in need thereof, e.g. for which such treatment is appropriate or indicated. The invention may be applied in the treatment of any disease or condition of the airways or lung which is susceptible to Ciclosporin therapy or for which Ciclosporin therapy is appropriate or indicated, including parasitic and/or mycotic disease such as coccidiomycosis and reversal of tumor resistance to chemotherapeutic drug therapy.

In particular the invention may be applied in the treatment of any disease or condition of the airways or lung requiring immunosuppressive or anti-inflammatory therapy, for example autoimmune or inflammatory diseases of the lungs, in particular inflammatory disease of the lungs comprising an autoimmune component as part of, or adjunct to, its etiology. Examples of such diseases include, for example, sarcoidosis and interstitial lung fibrosis. The method of the invention may also be applied to maintain lung transplant in lung or heart-lung transplantation patients.

Most particularly however, the invention is applicable to the treatment of inflammatory or obstructive airways disease and diseases of the airways and lungs involving inflammatory events accompanied by eosinophil and/or neutrophil accumulation, especially asthma and bronchitis.

The invention is applicable to the treatment of asthma of whatever type or genesis. It is applicable to both intrinsic and, especially, extrinsic asthma. It is in particular applicable to the treatment of allergic or atopic (i.e. IgE-mediated) asthma or non-atopic asthma, as well as e.g. bronchitic asthma, excercise induced asthma, occupational asthma, asthma induced following bacterial infection and other non-allergic asthmas. Treatment of asthma is also to be understood as embracing treatment of subjects, e.g. of less that 4 or 5 years of age, exhibiting wheezing symptoms, in particular at night, and diagnosed or diagnosable as "wheezy infants", an established patient category of major medical concern and now more correctly identified as incipient or early-phase asthmatics. This particular asthmatic condition is now generally referred to as "wheezy-infant syndrome".

In a specific embodiment, the invention is applicable to the treatment of asthma, e.g. of any type or genesis as set forth above, in subjects whose asthmatic status is either steroid dependent or steroid resistant.

The present invention is also applicable to the treatment of bronchitis or, especially, the treatment of chronic or acute airways obstruction associated therewith. In this regard the invention is applicable to the treatment of bronchitis of whatever type or genesis, including, for example, acute bronchitis, arachidic bronchitis, catarrhal bronchitis, chronic bronchitis, croupous bronchitis, phthinoid bronchitis and so forth.

The present invention is in addition applicable to the treatment of pneumoconiosis (an inflammatory, commonly occupational, disease of the lungs, frequently accompanied by airways obstruction, whether chronic or acute, and occasioned by repeated inhalation of dusts) of whatever type or genesis, including, for example, aluminosis, anthracosis, asbestosis, chalicosis, ptilosis, siderosis, silicosis, tabacosis and, in particular, byssinosis.

The present invention may also be applied to the treatment of eosinophil-related disorders of the airways (e.g. involving morbid eosinophilic infiltration of pulmonary tissues) including hypereosinophilia as it effects the airways or lungs as well as, for example, eosinophil-related disorders of the airways consequential or concomitant to Löffler's syndrome, eosinophilic pneumonia, parasitic (in particular metazoan) infestation (including tropical eosinophilia), bronchopulmonary aspergillosis, polyarteritis nodosa (including Churg-Strauss syndrome) and eosinophil-related disorders affecting the airways occasioned by drug-reaction.

Where appropriate, e.g. as applied to inflammatory or obstructive airways diseases as set forth above, the present invention, is to be understood as embracing both symptomatic and prophylactic modes of therapy, that is the treatment of disease symptoms, e.g. inflammation, as they occur (symptomatic therapy) as well as advance treatment to prevent or ameliorate occurrence of such symptoms or to restrict long term symptomatology (prophylactic therapy).

The term "treatment" as used in the present application and claims is to be interpreted accordingly as including both symptomatic treatment and prophylactic treatment, e.g. in the case of asthma, symptomatic treatment to ameliorate acute inflammatory events and associated bronchial exacerbation and prophylactic treatment to restrict on-going inflammatory status and to ameliorate future exacerbation.

By the present invention Ciclosporin is administered as CY-A/X-III. In practicing the invention, suitably, all or substantially all, e.g. at least 75%, preferably at least 85 or 90%, most preferably 95% or more of Ciclosporin administered will be administered as CY-A/X-III. Compositions for use in practicing the invention as hereinbelow described will thus also suitably be compositions in which all or substantially all of the Ciclosporin present is present as CY-A/X-III.

In practicing the present invention CY-A/X-III is administered via the pulmonary route, for example by inhalation from an appropriate dispenser device.

For this purpose CY-A/X-III may be employed in any suitable or convenient finely dispersed or finely dispersible form, capable of, e.g. adapted to or appropriate for, pulmonary administration, i.e. of administration into the airways and/or lungs. It may be administered by oral inhalation, for example in finely divided dry particulate form or in particulate form dispersed or distributed in any appropriate solid or liquid diluent or carrier medium (i.e. which is pulmonarily administerable or suitable for pulmonary administration) in which the integrity of the CY-A/X-III is maintained, i.e. in which the CY-A/X-III is substantially non-susceptible to dissolution or conversion into any other modification. Liquid media as aforesaid include e.g. volatile media, for example, compressed gasses.

For administration in dry particulate form, CY-A/X-III may be employed either as such (i.e. without any additive materials), in dilution with other appropriate finely divided inert solid carrier or diluent (e.g. glucose, lactose, mannitol, sorbitol, ribose, mannose, arabinose, saccharose, galactose, fructose or xylose), in coated particulate form (with or without additional inert carrier or diluent, for example, as aforesaid) or in any other appropriate form as known in the art for the administration of finely divided solids.

For pulmonary administration, CY-A/X-III will suitably be in particulate form having an aerodynamic mass median particle size ("AMMPS") of <10μ, preferably <5μ, more preferably of about 3μ or less. Appropriately at least 70%, preferably at least 80%, more preferably at least 85 or 90% of particles present in CY-A/X-III particulate preparations intended for pulmonary administration will have a particle size of <10μ, preferable <5μ, more preferably of about 3μ or less.

Minimum particle size will generally be less critical, though CY-A/X-III in particulate form having an AMMPS of <0.1μ, preferably <0.5μ, more preferably <1.0μ will normally be preferred. Suitably at least 75%, preferably at least 80 or 90% of particles present will have a particle size <0.1μ, preferably <0.5μ, more preferably <10μ.

For pulmonary administration CY-A/X-III having an AMMPS in the range of from 0.1, 0.5 or 1.0μ up to 10μ, preferably up to 5μ. Most preferably the AMMPS will be in the range of from 1.0μ to 5μ e.g. ca. 3.0μ.

As further explained hereinafter, it has in accordance with the present invention surprisingly been found that CY-A/X-III particulate systems, e.g. as described above, possess superior pulmonary delivery characteristics, e.g. in terms of quantity of material delivered into the airways, as compared with particulate systems comprising Ciclosporin in other solid form. In this connection it may be noted that the specific aerosolization/pulmonary delivery characteristics of the selected CY-A/X-III particulate material may, if desired, be varied by any of the techniques known or practiced in the art, for example by admixture with inert respirable or non-respirable particulate materials, such as hereinbefore set forth, of different average particle size or density.

As described in the aforementioned GB Patent Publication No. 2 211 848 A, CY-A/X-III is well adapted to the preparation of fine particulate systems complying with the above particle size requirements and such systems suitable for use in accordance with the present invention may be obtained by the techniques therein described, for example by direct microcrystallisation techniques and/or by comminution, e.g. grinding, milling, ultrasonication or other micronisation, of initially obtained, native CY-A/X-III crystal product. It may however be preferred to employ CY-A/X-III particulate preparations obtained directly by microcrystallisation techniques e.g. ultrasonication (and, if required, filtering out of larger crystals obtained, e.g. by filtering through a microfilter or screen) rather than comminution. The reason for this, as explained in the aforementioned UK patent publication, is the benefit achievable, e.g. in terms of avoidance of irritation or damage, by the use of microcrystals in native, non-fractured/non-abrasive state.

If desired, the surface characteristics of CY-A/X-III particulate material may be physically altered, e.g. to modify particle surface area, for example by deformation or other manipulation. By such methods modification of the Ciclosporin-delivery characteristics of the CY-A/X-III material within the lung or of the wettability or other characteristics of the CY-A/X-III material may be achieved. Such effects may for example be attained by subjecting CY-A/X-III material to ultrasonication or superficial chemical degradative techniques. One particular form of modification of particular interest in relation to the present invention comprises transformation into spheroidal particulate form as hereinafter described. As previously indicated, CY-A/X-III particulate material may, if desired, be subjected to particle coating with an appropriate coating or lubricating agent, to further restrict any potential irritative or abrasive action at the airways or lung surfaces.

Both dry and liquid galenic systems as described above may incorporate any further appropriate additives or ingredients as known in the art in relation to pulmonary administration, for example preserving agents, antioxidants, surfactant materials, buffering agents, tonicity adjusters, flavouring agents and the like, as well as propellants or other agents assisting distribution in inhalable form, for example assisting atomisation or nebulization or to prevent adhesion or clumping of particles.

Examples of galenic forms comprising CY-A/X-III suitable for use in accordance with the invention are provided in EXAMPLE 3 hereinafter.

Administration of galenic forms in accordance with the invention may be effected using any appropriate system as known in the art for delivering drug substances in dry or liquid form by inhalation, e.g. an atomiser, nebulizer, drypowder inhaler or like device. Preferably a metered dose inhaler ("MDI"), i.e. capable of delivering a pre-determined amount of drug substance at each actuation, will be employed. Such metered delivery devices are also well known in the art, and include e.g. breath actuated MDIs, MDIs with an extension chamber or spacer to reduce oropharyngeal deposition and breath operated dry powder delivery systems.

In accordance with the foregoing the present invention also provides:

B¹ A pharmaceutical composition for pulmonary administration, e.g. adapted or appropriate for pulmonary administration, comprising CA-A/X-III as active ingredient; for example B² A pharmaceutical composition as defined under B¹ wherein the CY-A/X-III is in dry particulate form or in particulate form distributed or dispersed in a pulmonarily administerable solid or liquid diluent or carrier medium.

The present invention further provides:

B³ A process for the production of a pharmaceutical composition as defined under B¹ or B² above, which process comprises preparing CY-A/X-III, for example CY-A/X-III produced in accordance with the methods described and claimed in GB patent publication no. 2 211 848(A), in particulate form, for example particulate form having size characteristics as herein before described, and, when required, distributing or dispersing said prepared particulate form in a pulmonarily amdinisterable solid or liquid diluent or carrier medium.

As previously noted, a common problem with administration of drugs by the pulmonary route, e.g. by inhalation, is retention of inhaled material within the buccal cavity and pharyngeal area and its ultimate delivery into the digestive tract. The risk is particularly high in asthmatics and other subjects whose lung function is compromised, whether by disease or other cause.

It is a particular and suprising finding of the present invention that the risk of systemic resorption, e.g. as a result of swallowing, and of consequential side effect, e.g. generalised immunosuppression or renal dysfunction, is significantly and unexpectedly reduced on pulmonary administration of Ciclosporin as CY-A/X-III, for example as compared with pulmonary administration of Ciclosporin in solution, in amorphous form or in other crystalline form. The present invention thus provides effective therapy for diseases of the airways and lungs with concomitant lowering or avoidance of systemic drug resorption/risk of Ciclosporin induced side effect. By the advantages this brings, the present invention may be anticipated to make pulmonary, e.g. inhaled, Ciclosporin therapy available to subjects to whom the benefits of therapy might otherwise be excluded on the basis of risk/benefit considerations. The invention thus extends the advantages of Ciclosporin therapy to a major patient population at need, for whom oral Ciclosporin therapy is inappropriate and for whom inhaled Ciclosporin therapy by other means is excluded or at best restricted.

Use of CY-A/X-III in accordance with the present invention also provides high local drug efficacy within the airways and lungs, i.e. high therapeutic benefit, again with the avoidance of substantial systemic resorption.

Use of CY-A/X-III in accordance with the present invention has also been found to be surprisingly advantageous in relation to the procedures or mechanics of pulmonary administration. Thus CY-A/X-III exhibits excellent inhaled delivery characteristics as determined in standard test models, e.g. as hereinafter described in EXAMPLE 4. Thus results are achievable with CY-A/X-III which appear not only superior to those achievable with Ciclosporin in e.g. amorphous or tetragonal crystal form, but superior to results obtainable in impinger experiments for inhalable drug substances in dry powder or particulate form generally. The present invention thus has the significant benefit of reducing inhaled Ciclosporin dosaging requirements.

Animal experiments using inhaled CY-A/X-III also indicate a reduced tendency to accumulation within and blockage of the smaller airways passages as compared for example with inhaled amorphous Ciclosporin/Ciclosporin in tetragonal crystal form.

Dosages of CY-A/X-III employed in practicing the method of the present invention will, of course, vary depending on the particular condition to be treated, the severity of the condition, the subject to be treated (e.g. in terms of body weight, age and so forth) as well as the effect desired. In general, for use in accordance with the invention, e.g. for use in treating inflammatory or obstructive airways disease, for example asthma, satisfactory results are obtained on administration of CY-A/X-III at a single dosage to the lungs of the order of from 3 to 10 mg/kg. A suitable dosage for larger animals, e.g. humans will thus be of the order of from 210 to 700 mg. For regular dosaging a suitable daily dosage for humans will be of the order of from 25 or 50 to 400 mg/day, more suitably from 50 to 300, e.g. from 100–200 mg/day.

Dosages will appropriately be administered from a metered delivery system, in a series of from 1 to 5, e.g. 1 or 2, puffs, administered once to four times daily. Dosages at each administration will thus be of the order of from about 6 or 12.5 to 100 mg, more suitably from 25 or 50 to 100 mg, e.g. administered 1× to 4× daily, with a metered delivery device, e.g. capable of delivering ca. 6 to 25 CY-A/X-III, per actuation and with 1× or 4× actuation at each administration.

In accordance with a yet further aspect of the present invention, it has now also and very surprisingly been found that crystalline Ciclosporin, including CY-A/X-III, may be induced to assume a spheroidal form without loss of crystal identity. More particularly it has been found that the outward appearance, e.g. of native Ciclosporin crystals or of crystal particles or fragments, can be transformed to provide a crystalline particulate product the individual particles of which are spheroidal. This transformation may, for example, be effected by subjecting crystalline Ciclosporin in non-spheroidal particulate form in disperse phase to conditions of elevated temperature and/or pressure.

The crystalline Ciclosporin starting material may comprise Ciclosporin in any crystal modification. The obtained spheroidal product comprises Ciclosporin in the self-same modification as the starting material. In particular the starting material may be CY-A/X-III or Ciclosporin in the form designated as CY-A/X-I. By "CY-A/X-I" as used herein and throughout the accompanying claims is meant Ciclosporin tetragonal (P4$_1$) crystal form.

[CY-A/X-I is described in the aforementioned GB patent publication no. 2 211 848 (A) and is described and claimed together with processes for its production, e.g. in Austrian patent specification no. 353,961. CY-A/X-I has a lattice a=b=13.8 Å, c=41.2 Å. The volume per asymmetric unit= 1974 Å$^3$. CY-A/X-I comprises ca. 2 molecules H$_2$O per Ciclosporin molecule and has a melting point at ca. 140°–150° C. CY-A/X-I exhibits the following x-ray powder diffraction data, e.g. as determined employing a Guinier-DeWolff II camera, using CuKα-radiation, X=1.542 Å.

| Line No. | d (Å) | Intensity |
| --- | --- | --- |
| 1. | 13.0 | VS |
| 2. | 11.4 | VS |
| 3. | 10.3 | VS |
| 4. | 9.7 | VS |
| 5. | 9.4 | VS |
| 6. | 8.25 | VS |
| 7. | 7.1 | S |
| 8. | 6.1 | M |

-continued

| Line No. | d (Å) | Intensity |
| --- | --- | --- |
| 9. | 5.85 | S |
| 10. | 5.6 | S |
| 11. | 5.25 | VS |
| 12. | 4.81 | S |
| 13. | 4.58 | S |
| 14. | 4.25 | M |
| 15. | 4.0 | M |
| 16. | 3.67 | M |
| 17. | 3.45 | M |

VS = very strong   S = strong   M = medium

CY-A/X-I may suitably be prepared by re-crystallisation from acetone, e.g. by dissolving amorphous Ciclosporin in ca. 3× the amount of acetone (e.g. 20 g Ciclosporin/50 ml acetone) with warming at 40°–50° C., followed by cooling to room temperature and completion of crystallasation at 5° C. for 4 hrs. and at −15° C. for 17 hrs. Collected crystals are suitably washed with acetone and dried under vacuum.]

The particulate starting materials for the transformation procedure may comprise native Ciclosporin crystals, e.g. CY-A/X-I or CY-A/X-III microcrystals, or fragmented or powdered, e.g. comminuted crystalline material. Transformation is effected in the disperse phase, i.e. with starting material particles dispersed or distributed throughout a larger volume. If the starting material is insufficiently dispersed, individual particles may coalesce during the transformation process, ultimately to produce a larger caked mass rather than the desired spheroidal particulate product.

Dispersion is suitably effected in a liquid medium in which the chosen crystalline material is non-soluble. Most suitably the starting material is dispersed in an aqueous medium, e.g. water. To further reduce coalescence during the transformation process, surfactants may be added. In general satisfactory results have been achieved, with avoidance of substantial coalescence, employing a dispersion of ca. 5% or less, preferably 1% or less, crystalline starting material in water. Alternative approaches to dispersion, for example in gaseous phase or under conditions of reduced gravity will be apparent to those skilled in the art.

The transformation itself is performed at elevated temperature and/or pressure. The precise conditions employed may be varied depending, e.g., on relative temperatures and/or pressures employed, the duration of the procedure and the particle size of the starting material. In general the temperature will be below, e.g. about 20° to 60° C. below, the normal melting point of the crystal modification undergoing transformation. Thus at normal or slightly elevated pressure, e.g. at pressures of from 1 to 2.5 atm., transformation of CY-A/X-I is suitably carried out at a temperature of from about 60° to 100° C., more preferably 70° to 90° C., e.g. about 80° C. and transformation of CY-A/X-III is suitably carried out at a temperature of from about 100° to 140° C., more preferably 110° to 130° C., e.g. about 120°, e.g. at 121° C.

The duration of the transformation procedure will also vary depending on the conditions employed. In general it has been found that a substantially spherical particulate product may be achieved with starting material having a particle size in the range of from ca. 1μ up to 20 or 50μ, employing conditions as set out above over a period of from 1 to 5, e.g. 2 or 3 minutes. If longer periods of time are to be used, agitation, e.g. stirring, to avoid coalescence will be appropriate.

The obtained product comprises particulate crystalline Ciclosporin, e.g. CY-A/X-I or CY-A/X-III, the particles being spheroidal, i.e. of spheroidal external appearance.

As will be seen, the product shown in FIGS. 2 and 3 is spherical or substantially spherical. The extent to which product particles approach the spherical may of course vary depending on the conditions of transformation, for example the duration of processing. Thus the surface may not necessarily be fully continuous or uniform. Shape may also be variable depending on the application of, e.g. sheering or gravitational, forces tending to extend or otherwise deform particles during transformation along one or more axes, to provide a product in which individiual particles are e.g. ellipsoid or oblate. The terms "spheroid" or "spheroidal" as used herein and in the accompanying claims are to be interpreted accordingly as embracing any form which is spherical or which tends towards or approximates the spherical, including e.g. elliptical and oblate spheroid forms and forms in which the surface is not wholly regular or uniform in appearance. Preferably however product particles will be spherical or substantially spherical. The surface of such particle will also preferably be regular or uniform or substantially regular or uniform.

Provided coalescence is avoided during the transformation process, the size (i.e. average diameter) of spheroidal particles produced will be determined by the particle size of the starting material used. If desired, average particle size may also be decreased in the course of transformation, e.g. by sonication or other high energy input. Alternatively particles of a particular desired size range may be recovered from initially obtained less homogenous material by the use of microfiltration or sieving procedures. To restrict coalescence it may be preferable to use as starting material, particulate material comprised of native Ciclosporin crystals rather than crystals which have been e.g. milled or ground.

As will be understood from the above description, the process of transformation is an essentially mechanical procedure. Neither the chemistry nor the essential crystal properties of the Ciclosporin is changed: only the outward appearance of the product is altered.

Crystalline Ciclosporin, e.g. CY-A/X-I or CY-A/X-III, in spheroidal particulate form, is a novel composition of matter. It is also advantageous in the preparation of novel galenic forms comprising Ciclosporin as active ingredient. In particular, being rounded in form, such particles will be inherently less likely to cause irritation or damage, e.g. abrasion of fine tissues or exacerbation of inflammatory response, than ground particulate or native microcrystalline material. Since spheroidal particles also tend to have a minimal surface:volume ratio, such particles may also be anticipated to provide slower Ciclosporin release at the site of delivery and hence a longer duration of therapeutic action. Accordingly in a yet further aspect the present invention provides:

$C^1$ Crystalline Ciclosporin, e.g CY-A/X-I or CY-A/X-III, in spheroidal particulate form;

$C^2$ A process for producing crystalline Ciclosporin in spheroidal particulate form which process comprises transforming Ciclosporin in non-spheroidal particulate form, e.g. Ciclosporin in native or fragmented (e.g. comminuted) crystal form, in disperse phase;

$C^3$ A pharmaceutical composition comprising crystalline Ciclosporin in spheroidal particulate form;

$C^4$ A method of effecting Ciclosporin therapy which comprises administering crystalline Ciclosporin in spheroidal particulate form; as well as $C^5$ Crystalline Ciclosporin in spheroidal particulate form for use as a pharamceutical.

Compositions as defined under $C^3$ above will suitably comprise crystalline Ciclosporin as defined in a condition suitable for pharmaceutical use, e.g. in sterile or substantially sterile condition.

Though Ciclosporin is present in compositions as defined under $C^3$ above in specified (i.e. crystalline and spheroidal particulate) form, the compositions themselves may be of any appropriate constitution. Compositions as defined under $C^3$ thus include solid forms, such as powders or granulates, semi-solid forms such as gels, creams and pastes, as well as liquid forms, e.g. comprising the defined Ciclosporin component suspended or dispersed in a pharmaceutically acceptable diluent or carrier in which the Ciclosporin component is non-soluble. Where enteral, e.g. oral administration, is intended, for example of CY-A/X-I, such compositions may also include compacted forms, e.g. tablets comprising CY-A/X-I in spheroidal particulate form with the individual particles press-formed into a cohesive mass, if necessary with the use of admixed pharmaceutically acceptable binding agents, diluents and the like. Alternatively the spheroidal particulate material may be filled or pressed into capsules.

Preferably the Ciclosporin component of compositions as defined under $C^3$ will consist entirely or substantially entirely of crystalline Ciclosporin in spheroidal particulate form.

Compositions as defined under $C^3$ above include forms suitable for topical administration, e.g. dermal or topical ophthalmic administration, as well as forms for parenteral administration, e.g. by injection, including sub-cutaneous or intra-muscular injection and, in particular, intra-lesional or intra-articular injection. Such injectible forms may include forms intended to have a prolonged duration of action, e.g. depot-forms for intra-muscular or intra-articular injection and which take advantage of the low surface:volume ratio of the defined active ingredient. Such forms may also include forms for enteral administration, though, in particular where the active ingredient comprises CY-A/X-III in spheroidal particulate form, these will be less preferred.

Compositions as defined under $C^3$ above, include compositions for pulmonary administration, e.g. of the type or comprising components hereinabove describe in relation to the present invention as defined under $B^1$ or $B^2$. In accordance with the teachings of the present invention compositions as defined under $C^3$ above for pulmonary administration will preferably comprise CY-A/X-III rather than e.g. CY-A/X-I, in particular having regard to the increased risk of systemic resorption when CY-A/X-I is employed.

The size of the particles employed in compositions as defined under $C^3$ above may vary depending, in particular, on the intended route of administration as well as the effect desired. Thus where intra-muscular injection for depot-effect is intended, use of larger size particles may be appropriate than in the case of compositions intended for intra-articular or, especially, pulmonary administration. In general the majority of particles will have an average diameter of <30 or <20μ, preferably <10μ, suitably <5μ, e.g. of about 3μ, whereby larger diameters will be tolerable, e.g. where intramuscular injection is intended. Appropriately at least 70%, preferably at least 80%, more preferably at least 85 or 90% of particles will conform to the above particle size requirements. Minimum particle size will be generally less critical, though systems comprising not more than 25%, suitably not more than 20% or 10%, of particles having a particle size of, <0.1μ, <0.3μ or <0.5μ will be preferred. Overall average particle size diameter for crystalline Ciclosporin as defined under $C^1$, or as used in compositions as defined under $C^3$, above will thus suitably lie within the range of from 0.1, 0.3 or 0.5μ up to 10, 20 or 30μ.

For pulmonary use the particle size for crystalline Ciclosporin as defined under $C^1$ or as used e.g. in compositions as defined under $C^3$, will suitably conform to the specifications hereinbefore described for pulmonary administration of CY-A/X-III particulate preparations generally, crystalline Ciclosporin, e.g. CY-A/X-III or CY-A/X-II, in spheroidal particulate form, having an AMMPS or average particle size diameter within the range of from 0.1, 0.5 or, preferably, 1.0 up to 10μ, preferably up to 5μ, e.g. of about 3.0μ, being particularly appropriate.

Compositions as defined under $C^3$ above may be prepared analogously to the methods described for, and employing any of the excipients disclosed for use in, the prepartion of compositions comprising CY-A/X-II as set forth in the aforementioned GB patent publication no. 2 211 848A, or as herein described in relation to the present invention as defined under $B^1$ or $B^2$ above or in the accompanying EXAMPLE 6.

The method of the present invention as defined under $C^4$ above may be applied in the treatment of any disease or condition for which Ciclosporin therapy is indicated or appropriate, in particular for effecting immunosuppression or anti-inflammatory therapy, e.g. for the treatment of any inflammatory disease or condition with an aetiology having an autoimmune component. The method may thus be applied for the maintainance of organ transplant, for example heart, lung, combined heart-lung, liver, kidney, pancreatic, bone-marrow, skin or corneal transplant, for the treatment of arthritis (for example rheumatoid arthritis, arthritis chronica progrediente and arthritis deformans), as well as for the treatment of autoimmune disease, e.g. any of the specific autoimmune diseases for which Ciclosporin therapy is known or has been proposed, for example autoimmune diseases as listed at page 2 of GB patent publication no. 2 211 848A. The method of the present invention as defined under $C^4$ above, in particular as it relates to CY-A/X-III in spheroidal particulate form, may also be applied in the treatment of any disease or condition of the airways or lungs as hereinbefore set forth or described in relation to the present invention as defined under $A^2$ above, in particular asthma. In relation to the present invention as defined under $C^5$ above, pharmaceutical use is to be understood as embracing use in the treatment of any disease or condition as aforesaid.

As previously indicated, use in accordance with the invention of crystalline Ciclosporin in spheroidal particulate form will be of particular advantage in the treatment of inflammatory diseases or conditions, e.g. of the joints or airways or lungs, as a means of avoiding or limiting further tissue damage or exacerbation of inflammatory event.

Dosages of crystalline Ciclosporin as defined under $C^1$ above employed in practicing the method of the present invention as defined under $C^4$ above will, of course, vary, e.g. depending on the route of administration, the condition to be treated, the severity of the condition, the subject to be treated, and the effect desired.

For pulmonary administration, e.g. for the treatment of inflammatory or obstructive airways disease, appropriate dosages will be of the same or similar order to those hereinabove described in relation to the pulmonary administration of CY-A/X-III generally. Suitable dosages or composition concentrations for dermal or topical ophthalmic administration or for administration by injection, e.g. for sub-cutaneous, intra-muscular or other parenteral injection, in particular intra-articular injection, will be of the same or similar order to those described in relation to the administration of CY-A/X-III via these routes in GB patent publication no. 2 211 848 A.

In a still further embodiment of the invention it has now also been found that Ciclosporin exhibits surprisingly high solubility in polychlorofluorohydrocarbon propellants. In particular it has unexpectedly been found that not only amorphous Ciclosporin but also CY-A/X-I and CY-A/X-III undergo ready dissolution in such propellants. This finding offers the possibility of administering Ciclosporin by the pulmonary route in solution, employing simple aerosol techniques as long known and practiced in the art. Accordingly the present invention additionally provides:

D) A pharmaceutical composition for pulmonary administration e.g. for the treatment of any disease or condition as hereinabefore described, in particular inflammatory or obstructive airways disease, e.g. asthma, which composition comprises Ciclosporin in solution in a polychlorofluorohydrocarbon propellant.

As will be appreciated, although the invention as defined under (D) provides a viable alternative for the pulmonary administration of Ciclosporin, for the reasons hereinbefore described as well as ecological considerations, this approach to pulmonary administration of Ciclosporin will generally be very much less preferred. Thus administration of Ciclosporin in solution will have none of the advantages of administration of CY-A/X-III, e.g. reduced risk of systemic side-effect, beneficial pulmonary delivery characteristics and so forth.

Polychlorofluorohydrocarbon propellants suitable for use in accordance with the invention as defined under (D) include any of those known in the art, e.g. as described in "Römpp Chemie Lexikon, 90, erweiterte und neubearbeitete Auflage", publ. Georg Thieme Verlag, Stuttgart+New York (1989) in the table at page 701, in particular trichlorofluoromethane, dichlorofluoromethane and 1,1,2-trichlorotrifluoroethane [$Cl_2FC-CClF_2$].

The concentration of Ciclosporin in compositions as defined under (D) will suitably be of the order of 2 mg per 90 µl polychlorofluorohydrocarbon or higher. For use, the defined compositions will be filled into and delivered from regular aerosol cans or bombs such as known in the art employing polychlorofluorohydrocarbon technology. Suitable daily dosages will be of the order of those hereinbefore described for the pulmonary administration of CY-A/X-III, whereby higher Ciclosporin delivery will generally be necessary to compensate for relatively poorer pulmonary delivery characteristics.

Utility of the present invention in each of its various aspects may be demonstrated in standard animal models or in clinic, e.g. in accordance with the procedures hereinafter described in the accompanying examples.

EXAMPLE 1: INFLUENCE OF CY-A/X-III ON ALLERGEN INDUCED EOSINOPHILIA IN THE GUINEA-PIG

Introduction

Eosinophilia is characteristic of the airways of asthmatic patients in mild as well as severe forms of the disease [Frigas and Gleich, J. Allergy Clin. Immunol., 77, 527–537, (1985)]. Eosinophilia is evident in bronchoalveolar lavage fluid from patients with atopic asthma and is intensified by allergic (IgE-mediated) reactions. Eosinophilia of the airways is also pronounced in non-atopic asthma and can be intensified by procedures in which IgE is not implicated (e.g. exposure to aspirin).

1.1 Pulmonary Administration

Male Himalayan spotted guinea-pigs of ca. 300 g are sensitized to ovalbumin (OA) by i.p. administration of 1 ml of a suspension of 10 µg OA, 0.25 ml B. pertussis vaccine and $Al(OH)_3$ (2.0 mg) in saline (0.9% w/v). The procedure is repeated 2× at 3 weeks intervals and animals used 1 week after the last injection.

Challenge is effected by administration of nebulised OA (0.01%) in saline solution discharged into an exposure chamber, following dilution with clean air. Animals are exposed to OA by nose-only inhalation for 60 mins.

In untreated (control) animals OA challenge causes an increased influx of eosinophils (5–10 fold) and other inflammatory cells into the airway lumen of sensitised guinea pigs, as determined by broncheolar lavage and cell counting performed as follows:

Animals are killed by i.p. injection of pentobarbitone (100 mg/kg). The trachea is exposed and cannulated. Successive aliquots (10 ml) of $Ca^{++}$ and $Mg^{++}$ free Hank's balanced salt solution containing bovine serum albumin (0.3%), EDTA (10 mM) and HEPES (10 mM) are introduced into the lungs and immediately aspirated by gentle compression of the lung tissue. The procedure is performed 6×. Aspiration fluid is pooled at room temperature in Falcon plastic tubes (60 ml). Fluid recovered from the six washes normally exceeds 50 ml (85%). The cell suspension is centrifuged (200 g for 10 minutes); the supernatant is discarded and the cell pellet resuspended in 1 ml of supplemented Hank's balanced salt solution. Total cell counts in pooled eluates are determined using an automatic cell counter. For differential cell count, 10 µl of the 1 ml cell suspension is added to 190 µl of Turk's fluid and counts made from smears stained with Diff-Quick. Cells are identified and counted under oil immersion. A minimum of 500 cells are counted per smear and the total population of each cell type calculated.

For determination of activity on inhalation, micronised test substance is administered via nose-cone with delivery from a brush feed micronising jet mill powder aerosol generator as described in Bernstein et al. "Aerosols: Science, Technology and Industrial Application of Airborne Particles", Extended Abstract, eds. B. Y. H. Lin et al., Elsevier Science, New York, 1984. Test animals are restrained within flow-past, nose-only exposure chamber, no more than 15 mins. prior to challenge.

In the above test model administration of micronised CY-A/X-III [particle size ca. 89% <3µ], results in substantial reduction in eosinophil and neutrophil counts at total inhaled dosages of from 3.0 to 10.0 mg/kg as compared with untreated controls.

Administration of a micronised 1:1 mixture of amorphous Ciclosporin and CY-A/X-I [particle size ca. 90% <3µ] provides comparable results.

In this test model CY-A/X-III is thus established as being equipotent or substantially equipotent to amorphous Ciclosporin:CY-A/X-I when administered by inhalation.

1.2 Oral Administration

Testing is carried out in accordance with the procedures described above but with test substance administered orally in suspension in carboxymethyl cellulose 15 mins. prior to challenge.

In this test model evidence of reduction of eosinophil and neutrophil infiltration is only apparent on oral administration of CY-A/X-III at doses in excess of 60 mg/kg. Unequivocal inhibition is only observed at doses in excess of 100 mg/kg e.g. between 100 and 240 mg/kg.

In contrast, unequivocal inhibition is observed on oral administration of a 1:1 mixture of amorphous Ciclosporin and CY-A/X-I at doses of from 20 mg/kg upwards, e.g. between 20 and 80 mg/kg.

1.3 Conclusion

Comparison of efficacy between CY-A/X-III and amorphous Ciclosporin:CY-A/X-I administered by the oral route indicates marked reduction in systemic resorption (ca. 3-fold) in the case of CY-A/X-III. Since dosages of CY-A/X-III required for efficacy by the inhaled route are substantially (ca. 10-fold) lower than those required for efficacy via the oral route effect of inhaled CY-A/X-III can not be attributed to resorption following in advertant oral administration in the course of the test procedure.

EXAMPLE 2: SYSTEMIC RESORPTION CHARACTERISTICS

Ciclosporin is administered to male guinea-pigs (Dunkin-Hartley) of ca. 300–400 g by the oral route, in CY-A/X-III form or in the form of a 1:1 mixture of amorphous Ciclosporin and CY-A/X-I. In each case administration is in gel suspension in carboxymethyl cellulose. Test animals are divided into groups, with individual groups receiving Ciclosporin as CY-A/X-III at 4, 20 and 40 mg/kg (groups 1 to 3), or amorphous Ciclosporin-CY-A/X-I at 4, 20 and 40 mg/kg (groups 4 to 6). Blood samples are taken prior to administration of Ciclosporin and 1, 2, 4 and 6 hours after administration and screened for Ciclosporin levels using standard monoclonal RIA assay techniques.

Significant systemic resorption is recorded for groups (4) to (6) following Ciclosporin administration as evidenced by determined Ciclosporin blood levels. In groups (1) to (3) no or substantially reduced recorded resorption is recorded past administration as compared with groups (3) and (4).

EXAMPLE 3: INHALABLE GALENIC PREPARATIONS

In each of the following examples, CY-A/X-III is employed in fine particulate form having an average AMMPS of from 0.5 to 10.0, preferably to 5.0µ, preferably of ca. 3.0µ or less. Typically, native CY-A/X-III crystals prepared in accordance with the procedures of Examples 1 or 2 of the aforementioned UK patent publication 2 211 848 and subsequently micronised in a colloidal or air-jet mill to give a micronised product having an average AMMPS size of ca. 9.9µ, 5µ, 3µ or less, e.g. of 2–3µ. Alternatively, the material is native, microcrystalline CY-A/X-III having an average AMMPS crystal/particle size of from 2–10µ, prepared by effecting crystallisation with application of ultrasonication at from ca. 10,000 to 30,000 cycles per sec, again as described in UK patent publication 2 211 848.

| 3.1 | CY-A/X-III | 25 mg |
| --- | --- | --- |

The CY-A/X-III fine particulate material is filled into a hard gelatin capsule for insertion in and delivery from, a conventional dry powder inhalation device.

| 3.2 | a) CY-A/X-III | 20 mg |
| --- | --- | --- |
|  | b) lactose (100 mesh) | 5 mg |
|  | Total | 25 mg |

Components (a) and (b) are intimately mixed in conventional manner and the resulting, homogeneous powder product sieved and filled into a hard gelatin capsule for use as indicated under 3.1 above.

| 3.3 | a) CY-A/X-III | 150.0 mg |
| --- | --- | --- |
|  | b) purified H$_2$O | 10.0 ml |
|  | c) Disodium hydrogen phosphate | 41.4 mg |
|  | d) Citric acid | 8.0 mg |
|  | e) NaCl | 74.7 mg |
|  | f) Soya lecithin | 4.0 mg |
|  | Total | 288.1 mg |

Component (a) is suspended in an aqueous system comprising components (b) to (f) in conventional manner and the obtained suspension filled into the reservoir of a conventional nebulizer device.

Compositions as described above are useful for pulmonary administration, e.g. in the treatment of asthma.

EXAMPLE 4: INHALATION DELIVERY CHARACTERISTICS OF CY-A/X-III PARTICLE PREPARATIONS

The trial is conducted employing a twin impinger device as described in Hallworth et.al. J. Pharm. Pharmacol, 39, 966–972 (1987) and methodology in accordance with The British Pharmacopoeia 1988, Vol. II, Appendix XVII C (A 204–A 207). Trial material comprises a jet-milled CY-A/X-III preparation with 90% of particles having a particle size <10µ. Trial material is delivered to the impinger device from a size 3 capsule employing a Boehringer dry powder applicator.

Results for CY-A/X-III material show surprisingly high delivery to the lower impinger or impingement chamber (cf. Hallworth and British Pharmacopoeia loc. cit.) corresponding to high level delivery to the lung. Thus in one series of trials ca. 42% of material is recovered from the lower impinger chamber.

Improvement of CY-A/X-III delivery characteristics may be achieved by admixture of the trial material with other inert, fine particulate, inhalable or non-inhalable diluents (e.g. such as hereinbefore described) so as to increase or decrease the average particle size or density for the CY-A/X-III+diluent admixture.

EXAMPLE 5: PREPARATION OF CY-A/X-III IN SPHEROIDAL PARTICULATE FORM

CY-A/X-III in particulate form having a particle size ranging from ca. 3.0 to 40µ and in which the particles are comprised of native CY-A/X-III microcrystals in 1% aqueous suspension are heated in an autoclave at 120°–121° C. at ca. 2.5 Atm for 2 to 3 minutes. The obtained suspension is filtered and the particles dried. The product particles comprise CY-A/X-III in substantially spherical form with particle diameters within the range of from ca. 3.0 to 40µ.

By repeating the process with a particulate CY-A/X-III starting material comprising sonicated CY-A/X-III microcrystals having a particle size of from 1.0 to 5.0µ and an average particle size of ca. 3.0µ and with agitation or disruption, e.g. stirring, of the suspension in the course of autoclaving, CY-A/X-III spheroidal particulate form is obtained having an average particle size of ca. 3.0µ.

Equivalent results are obtained on replacing the starting material with CY-A/X-I in non-spheroidal particulate form.

EXAMPLE 6: GALENIC PREPARATIONS COMPRISING CY-A/X-III OR CY-A/X-I IN SPHEROIDAL PARTICULATE FORM 6.1 Form for Intra-Lesional Injection A suspension of CY-A/X-III in spheroidal particulate form with a particle diameter in the range of from ca. 3.0 to 40μ, prepared in accordance with the procedures of Example 5 is prepared under sterile conditions employing the following ingredients.

| a) Spheroidal particulate CY-A/X-III | 20.0 mg |
|---|---|
| b) Plysorbate 80 | 4.0 mg |
| c) Sodium carboxy methyl cellulose | 5.0 mg |
| d) NaCl | 9.0 mg |
| e) Benzyl alcohol | 9.0 mg |
| f) H$_2$O injection grade to an end vol. of | 1.0 ml |

The obtained suspension is filled into injection ampoules for intra-lesional injection, useful in the treatment of psoriasis.

6.2 Injectible Form for Intra-Articular Injection

An injectible form comprising CY-A/X-III in spheroidal particulate form with a particle diameter in the range of from 1.0 to 5.0μ and prepared in accordance with the procedures of Example 5 is prepared under sterile conditions employing the following ingredients:

| a) Spheroidal particulate CY-A/X-III | 10.0 mg |
|---|---|
| b) Sodium carboxy methyl cellulose | 10.0 mg |
| c) Na EDTA | 2.0 mg |
| d) H$_2$O injection grade to an end vol. of | 1.0 ml |

The obtained composition is filled into ampoules, useful for intra-articular injection in the treatment of rheumatoid arthritis.

6.3 Inhalable Forms for Use e.g. in the Treatment of Asthma

Compositions are prepared analogous to Examples 3.1 to 3.3 but employing CY-A/X-III in spheroidal particulate form with an average AMMPS in the range of from 1.0 to 5.0μ, preferably ca. 3.0μ or less, and prepared in accordance with the procedures of Example 5. The compositions are sieved and, e.g. filled into a hard gelatin capsule for insertion in and delivery from a conventional dry powder inhalation device, useful e.g. for asthma therapy.

Equivalent compositions to those described under 6.1 to 6.3 above may be prepared but with substitution of the CY-A/X-III component with CY-A/X-I in spheroidal particulate form.

EXAMPLE 7: PREPARATION OF AEROSOL COMPOSITION COMPRISING CICLOSPORIN IN SOLUTION IN A POLYCHLOROFLUORO-HYDROCARBON PROPELLANT MEDIUM 1 p.p.w. of Ciclosporin in the form of a 1:1 mixture of amorphous Ciclosporin and CY-A/X-I or as CY-A/X-III is added to a mixture comprising 0.65 p.p.w. Span 85, 21.22 p.p.w. Frigen 113 and 21.13 p.p.w. Frigen 11/12. The Ciclosporin component dissolves in the Frigen components to provide a solution which is filled into the reservoir of a conventional inhaler device capable of delivering e.g. 1.0, 2.0, 5.0 or 10.0 mg Ciclosporin at each actuation and useful, e.g. in asthma therapy.

Efficacy of CY-A/X-III employed in accordance with the present invention, avoidance of systemic resorption and other advantages as hereinbefore set forth may also be demonstrated in clinical trials, for example, carried out as follows:

CLINICAL TRIAL

Trial subjects are selected from patients diagnosed as exhibiting chronic asthma, and including patients who require regular ingestion of glucocorticosteroid drugs to achieve disease control. Subjects receive CY-A/X-III at doses of from between 50 and 200 mg, e.g. 100 mg/day, administered in divided doses 3 to 4× daily. CY-A/X-III is administered in particulate form comprising:

a powder preparation derived from jet-milled native microcrystalline CY-A/X-III material having an AMMPS in the range of from 0.5 to 5.0μ, typically of ca. 3.0μ; or CY-A/X-III in spheroidal particulate form, e.g. prepared in accordance with the procedures of Example 5 and having an AMMPS in the range of from 1.0 to 5.0μ, typically of ca. 3.0μ.

CY-A/X-III is delivered by the pulmonary route from a conventional dry powder, metered dispenser device. The following parameters are measured at predetermined intervals throughout the course of the trial: forced expiratory volume (FEV.), peak expiratory flow rate (PEFR) and, in subjects who are sensitive to specific antigens, airways obstruction following inhalation of test dosages of antigen. In addition, required steroid maintainance dosage or usage of other anti-inflammatory anti-asthma drug therapy is monitored throughout the trial. Broncheolar lavage (BAL) is performed in participating subjects prior to entry into the trial and at the completion of the trial as well, in the case of longer trial protocolls, during the course thereof. Lavage samples are screened for the incidence of inflammatory cells in particular eosinophils. Blood samples of participating subjects are taken prior to, during the course of (e.g. at 14 day intervals) and on trial completion. All samples are monitored for regular parameters as well as for whole blood Ciclosporin concentrations (using standard monoclonal antibody RIA).

Results for subjects receiving CY-A/X-III are compared with results for parallel groups of patients of comparable asthmatic status, receiving regular therapy only. Alternatively the trial is performed in double blind manner in parallel patient cohorts receiving (i) CY-A/X-III as described or (ii) placebo powder material only. Individual trials are designed to proceed over periods of from 1 week and less up to 1 to 6 months where steroid usage is to be monitored.

Subjects receiving CY-A/X-III in clinical trials designed as aforesaid exhibit improvement in measured lung function parameters, a reduction in BAL inflammatory cell count, as well as recorded progressive incremental reduction of steroid usage or usage of xanthine or other anti-inflammatory therapies during the course of the trial as compared with control groups not receiving CY-A/X-III or receiving placebo. Ciclosporin blood levels recorded in groups receiving CY-A/X-III are relatively low to negligible. CY-A/X-III therapy is well tolerated with no significant incidence of recorded side effect or untoward influence on blood-serum parameters. Application of CY-A/X-III is unproblematic as determined by both independent observation and subjective patient reports.

We claim:

1. A method of administering ciclosporin to a subject in need of ciclosporin therapy, which comprises administering to said subject orthorhombic crystalline CY-A/X-III having crystal lattice dimensions of a=12.7 Å, b=15.7 Å, c=36.3 Å, and a volume per asymmetric unit=1804 Å$^3$ by the pulmonary route in an amount effective for said therapy.

2. A method according to claim 1 of treating a disease or condition of the airways or lung requiring ciclosporin therapy, which comprises administering to a subject in need of said treatment orthorhombic crystalline CY-A/X-III by the pulmonary route in an amount effective for said treatment.

3. A method according to claim 1 in which the CY-A/X-III is administered in a pulmonary pharmaceutical composition comprising CY-A/X-III in dry particulate form or in particulate form distributed or dispersed in a pulmonarily administerable solid or liquid diluent or carrier.

4. A method according to claim 3 in which the CY-A/X-III in particulate form has an AMMPS of less than 10µ.

5. A method according to claim 3 in which the CY-A/X-III in particulate form has an AMMPS of less than 5µ.

6. A method according to claim 3 in which the CY-A/X-III in particulate form has an AMMPS of from 1 to 5µ.

7. A method according to claim 1 in which 25 to 400 mg of CY-A/X-III is administered daily.

8. A method according to claim 1 in which 50 to 300 mg of CY-A/X-III is administered daily.

9. A method according to claim 1 in which 100 to 200 mg of CY-A/X-III is administered daily.

10. A method according to claim 2 for the treatment of inflammatory or obstructive airways disease.

11. A method according to claim 10 for the treatment of asthma.

12. A method according to claim 1 which method comprises pulmonary administration of CY-A/X-III in spheroidal particulate form.

13. A method according to claim 2 which method comprises pulmonary administration of CY-A/X-III in spheroidal particulate form.

* * * * *